United States Patent [19]

Laplanche

[11] 4,237,890
[45] Dec. 9, 1980

[54] FASTENER MEANS FOR DISPOSABLE DIAPERS AND PROCESS OF MANUFACTURE

[75] Inventor: Pierre Laplanche, Turckheim, France

[73] Assignee: S.A. Beghin-Say, France

[21] Appl. No.: 1,849

[22] Filed: Jan. 8, 1979

[30] Foreign Application Priority Data

Jan. 6, 1978 [FR] France .................................. 78 00341

[51] Int. Cl.[3] ............................................. A61F 13/16
[52] U.S. Cl. ............................ 128/287; 128/DIG. 30; 427/208; 428/261
[58] Field of Search ................ 128/284, 287, DIG. 30; 427/207 R, 207 B, 207 C, 208; 428/261, 343

[56] References Cited

U.S. PATENT DOCUMENTS

| | | | |
|---|---|---|---|
| 3,800,796 | 4/1974 | Jacob | 128/DIG. 30 |
| 3,874,386 | 4/1975 | Kozak | 128/DIG. 30 |
| 3,920,018 | 11/1975 | Schaar | 128/DIG. 30 |
| 3,930,503 | 1/1976 | Tritsch | 128/DIG. 30 |
| 4,024,312 | 5/1977 | Korpman | 128/DIG. 30 |
| 4,050,121 | 9/1977 | Richman | 128/DIG. 30 |

FOREIGN PATENT DOCUMENTS

| | | | |
|---|---|---|---|
| 2418209 | 10/1975 | Fed. Rep. of Germany ... | 128/DIG. 30 |
| 48-49542 | 7/1973 | Japan .............................. | 128/DIG. 30 |

*Primary Examiner*—C. Fred Rosenbaum
*Attorney, Agent, or Firm*—A. W. Breiner

[57] ABSTRACT

Fastener means for disposable diapers comprising a band or strip of material folded in the shape of an "S" comprising a first end zone, a central zone, and a second end zone; at least the central zone being elastic and the side of the second zone facing the central zone being coated with a pressure-sensitive adhesive which in turn is covered with a protective material which in turn is connected to the central zone by a continuous or discontinuous row of glue parallel to the S-fold of the fastener. The fastener can be easily manufactured on an industrial scale; can be conveniently affixed to a diaper during the manufacture of the diaper; permits convenient fastening of the front and rear parts of a disposable diaper, and accommodates for the movements of a baby wearing the diaper.

18 Claims, 8 Drawing Figures

FASTENER MEANS FOR DISPOSABLE DIAPERS AND PROCESS OF MANUFACTURE

This invention is directed to a fastener particularly applicable for the fastening of the front and rear parts of a disposable diaper. The invention is also directed to a process for manufacturing the fasteners.

Disposable diapers presently are made of absorbing materials comprising a padding of cellulosic fibers placed between an impermeable support sheet (generally of polyethylene) and a permeable sheet (generally a non-woven, made by dry or wet processes)—permeability or impermeability being with respect to liquids, i.e., urine, coming in contact with the baby's skin. The disposable diaper is suitably placed or positioned on the baby and maintained around the baby's waist by adhesive fasteners, one end being firmly fixed to the support sheet at its upper end and the other end, being coated with an adhesive protected by a silicone-treated paper, remaining free. When it is time to use the diaper, the silicone-treated paper is removed and the freed adhesive part is applied against the upper rear part of the support sheet. The aforesaid arrangement is not completely acceptable in that the diaper front and rear parts are connected together fairly rigidly. Accordingly, the baby's movements frequently cause the fasteners to become unstuck.

Attempts have been made, therefore, to make the fasteners elastic. Specifically, U.S. Pat. No. 3,920,018 describes a diaper essentially rectangular before use, which includes two opposite pairs to be placed around the baby's waist. Elastic means are fastened to one of the diaper parts which can be tied around the baby's waist. The elastic means essentially comprise an extending loop. It is difficult to make such fasteners in an industrial process. Further, when manufacturing the diapers, the fasteners are located outside the surface bounded by the diapers. Accordingly, it is difficult or impossible to achieve high rates of production of the finished diaper.

French Pat. No. 2,137,855 describes a disposable diaper comprising at least one fastener having a semi-elastic band, with an elastic central section which can freely extend and which is sandwiched between two non-extending end sections. One of the end sections is fastened to one of the diaper edges at the level of the infant's waist, and the other free end is coated with a pressure-sensitive adhesive. Under a proposed variation, the two free end sections are connected together and may be separated by tearing along a perforated line. The fasteners as described can only be used on a diaper of a given size, requiring the manufacturer to provide several fastener models, i.e., to accommodate diapers of different size. Furthermore, the system of the patent can only be used for diapers folded in a certain manner.

An S-folding fastener is described in U.S. Pat. No. 3,874,386. The fastener comprises one end which is to be fixed to the diaper, a central section, and a free end folded so that the free end and the central section are located above the fixed end, the lower side of the free end being temporarily bonded by a pressure-sensitive adhesive to the lower side of the central section. French Pat. No. 2,267,058 describes a fastener similar to the fastener described in U.S. Pat. No. 3,874,386, and comprises an adhesive closure for diapers in the form of a strip coated with self-adhesive and bonded to the diaper. One of the sides of the strip is treated with an anti-adhesive agent. The strip is in three sections joined by the folding lines, two of the sections—one of which is at the edge of the strip—being provided on their opposite side with a pressure-sensitive adhesive. The strip is folded in the shape of an "S" whereby one of the adhesive sections adheres to the diaper. The other section makes contact with the non-adhesive part of the strip. Furthermore, an adhesive point is provided between the non-adhesive sides of the two sections. The S-shaped fasteners described in the aforesaid patents are not completely acceptable in that they cannot extend.

Accordingly, the prior state of the art suggests to the manufacturer of diapers either elastic fasteners which cannot be mass-produced or mass-produced only with difficulty, or S-folded fasteners which are non-elastic.

A primary object of the present invention, therefore, is to provide an S-folded fastener characterized in that it comprises a first end zone, a central zone, and a second end zone. The side of the second zone facing the central zone is covered with a pressure-sensitive adhesive itself covered by a protective element which in turn is connected to the central zone. In one embodiment of the invention, the various zones are elastic and the central zone is connected to the first zone by dots or rows of glue arranged so that the zones are kept parallel. In another embodiment of the invention, only the central zone is elastic, the first and second zones being substantially nonelongating. The various zones of the fastener according to this second embodiment are distinct sections or elements connected among themselves by rows of glue arranged on the same side of the central zone, or else on the sides opposite the central zone near its lateral edges. The central zone of the fastener is made of an elastic material such as a short elastic band and the two ends thereof are glued to two strips or bands of paper.

The present invention also relates to a manufacturing process for producing diaper fasteners having an "S" shape comprising, in sequence, the following steps:

(a) applying a row of glue to one face of an elastic strip near a lengthwise edge;

(b) applying a row of glue near each lengthwise edge to the other side of the strip treated in (a);

(c) combining the strip treated in (b) with first and second tapes of paper coated with a pressure-sensitive adhesive which in turn is covered with a protective paper, the face of the strip provided with a single row of glue making contact with the side without an adhesive of the first tape of paper; and the side provided with two rows of glue making contact with the protective paper covering the coated side of the second tape of paper;

(d) winding the layered product of (c); and (e) cutting the layered structure into a set of fasteners at the time of manufacturing diapers.

An alternative embodiment of the S-shaped type of fastener is manufactured by a process comprising the following steps in sequence:

(a) applying three rows of glue to the side of an elastic strip,
 a first row very close to a lengthwise edge,
 a second row near the first row,
 a third row near the other lengthwise edge;

(b) applying a row of glue to the other side of the strip treated in (a) very close to the lengthwise edge opposite to the side containing the first and second rows of glue;

(c) combining the strip treated in (b) with two tapes of paper of which one side is coated with a pressure-sensitive adhesive itself covered with a protective paper so that each lengthwise edge of the strip is firmly fixed to the respective edge of one paper tape on the side which is coated with a pressure-sensitive adhesive;

(d) folding the structure obtained in (c) into an "S" shape and winding the tape; and (e) cutting the structure obtained in (d) into a series of fasteners when fabricating diapers.

The invention will be better understood in relation to the attached drawings which are illustrative of preferred embodiments of the invention without limiting its scope.

Figure 1:
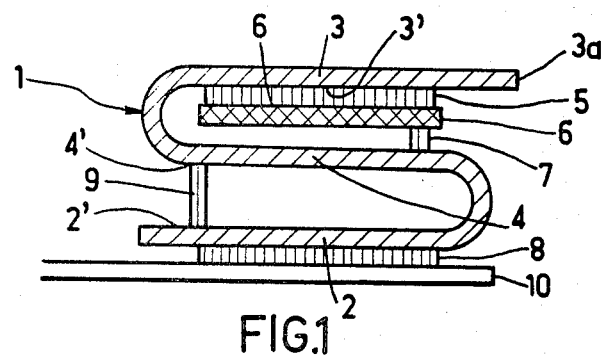
FIG. 1 is a cross-section of an S-folded fastener of the invention and comprising a single elastic strip.
Figure 2:
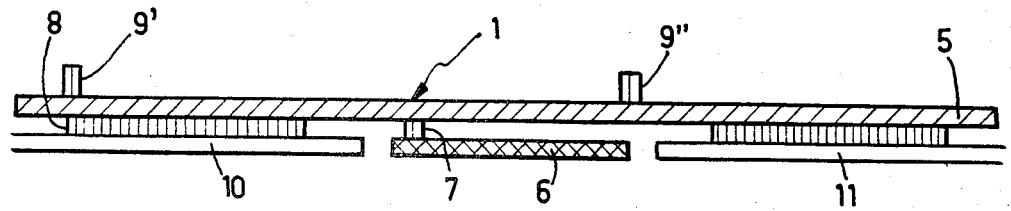
FIG. 2 is a cross-section of a fastener of FIG. 1 when in use to maintain a diaper in the desired form.

Referring first to FIGS. 1 and 2 of the drawing, an elastic strip 1 is folded into the S-shape comprising a first end zone 2, a central zone 4, and a second end zone 3. Side 3' of zone 3 opposite central zone 4 is coated only in its median part with an adhesive 5, of the pressure-sensitive type, which in turn is covered with a protective element 6 which in turn is connected to central zone 4 by dots and/or rows of glue 7. Side 6' of protective element 6 is treated with a silicone compound so that its bonding to zone 4 will be stronger than its bonding to zone 3. In use, the first zone 2 is mounted on the upper edge 10 of the diaper by means of the pressure-sensitive adhesive 8. In order to keep zones 2 and 3 parallel or in alignment, rows of glue 9 are used to connect sides 2' and 4' of zones 2 and 4, respectively. As shown, zone 3 is longer than zone 2 and comprises an end 3a of which the lower side is free of adhesive. When the diaper is to be placed on a baby and fastened around the baby's waist, it is only necessary to take the fastener by the end 3a and pull with a minimum of effort to detach zone 3 from the protective paper 6. The row of glue 9 is divided into rows 9' and 9" and the protective paper remains fixed to zone 4 because of the rows of glue 7. The zone 3 by means of its pressure-sensitive adhesive 5 is fixed to the rear edge 11 of the diaper.

Figure 3:
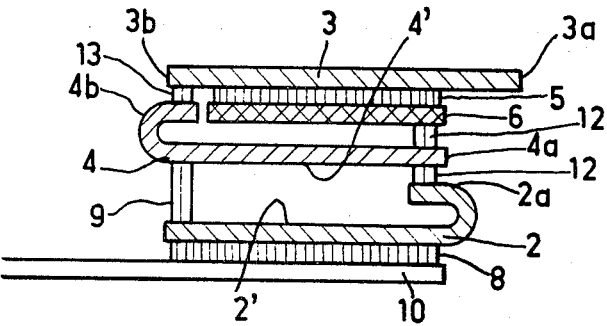
FIG. 3 is a cross-section of the fastener of the invention comprising a central elastic zone, and first and second non-elastic end zones.
Figure 4:
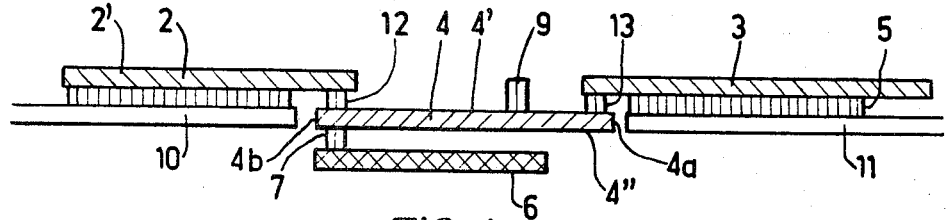
FIG. 4 is a cross-section of the fastener of FIG. 3 when in use to maintain a diaper in the desired shape.

In another embodiment of the invention as shown in FIGS. 3 and 4, zones 2, 3, and 4 are distinct sections or elements. Only zone 4 is elastic. Zones 2 and 3 are non-elongating. The end 3b of zone 3 is connected with end 4b of zone 4 by the rows of glue 13. As shown in FIG. 3, bent-back end 2a of zone 2 is connected to a lateral edge 4a of zone 4 by rows of glue 12. Upper side 2' of zone 2 preferably is treated with a silicone compound. The connection between protective element 6 and zone 4 by rows of glue 7 is stronger than that between said element 6 and zone 3, which latter is covered with a pressure-sensitive adhesive 5 because of the treatment or surface 6', as in the embodiment of FIG. 1, with a silicone compound. When the fastener is to be used—by pulling on end 3a, element 6 becomes unglued from zone 3, the rows of glue 9 being completely detached off surface 2' because of the silicone treatment, while element 6 remains fixed to zone 4. Zone 3 is then fixed to edge 11 of the diaper. It will be noted that in this embodiment the rows of glue 13 and 12 are all located on side 4' of elastic zone 4 near its lateral edges 4a and 4b. When the fastener is in its pre-use position, end 4b of zone 4 is folded into a "C."

Figure 5:
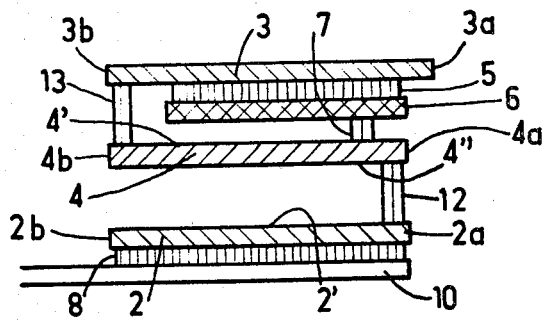
FIG. 5 is another variation of the fastener in a preferred embodiment of the invention.
Figure 6:
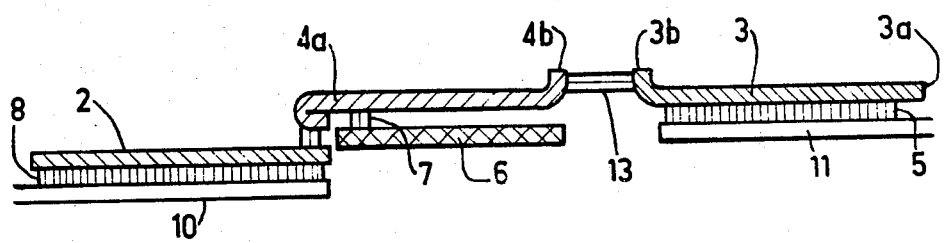
FIG. 6 is a cross-section of the fastener of FIG. 5 when in use to maintain a diaper in the desired shape.

Another preferred embodiment of the invention is shown in FIGS. 5 and 6. The rows of glue 12 and 13, respectively, connecting zones 2,4 and 3,4 are located near the ends 4a,4b of zone 4 on sides 4" and 4', respectively, of zone 4. The constituent elements 2, 3, and 4 of the fastener are parallel bands and in this embodiment it is unnecessary to connect end 4b of zone 4 to end 2b of zone 2; nor is it necessary to treat side 2' of zone 2 with a silicone compound. When such fastener is in use—by pulling on end 3a of zone 3, the protective element 6 is unglued from zone 3. End 4a of zone 4 bends back and the ends 4b of zone 4 and 3b of zone 3 curve slightly. Protective element 6 remains fixed to zone 4 because of the rows of glue 7. In this manner S-folded fasteners with a central elastic zone are obtained which allow easy diaper manufacture in that they are not outside the surfaces of the diaper. Further, the S-folded fastener can be used on all types of diapers regardless of size and shape. Preferably zones 2 and 3 will be made of paper, though they also may be made of cloth, plastics, or any other known suitable material. Their length may vary as desired, but preferably are from about 2 to 4 cm and their width from about 1 to 4 cm. Zone 4, preferably an elastic strip, can also vary as desired, but preferably will be between about 2 and 4 cm long and between about 1 and 4 cm wide.

Figure 7:
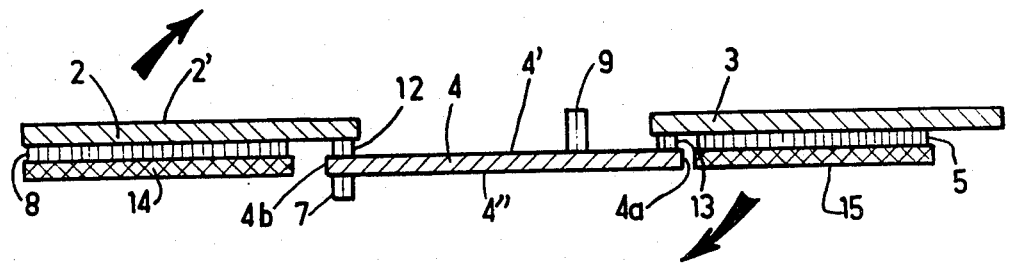
FIGS. 7 and 8 illustrate the fasteners of FIGS. 3 and 5, respectively, when being fabricated.

The manufacturing process for S-folded fasteners as shown in FIG. 3 can easily be followed in relation to FIG. 7. The process is as follows:

(a) three rows of glue are deposited on side 4' of strip 4,
  a first row 13 immediately along the lengthwise edge 4a,
  a second row 9 indented from, but near row 13,
  a third row 12 immediately against the lengthwise edge 4b;

(b) a row of glue 7 is deposited on side 4" of strip 4 near the lengthwise edge 4b;

(c) the strip treated in (b) is combined with two tapes of paper 2 and 3, respectively, coated with adhesive pressure-sensitive layers 8 and 5 protected by silicone-treated papers 14 and 15. Side 2' of paper 2 is also treated with a silicone compound.

The structure so obtained is folded in the direction of the arrows so as to impart an S-shape to the structure. The material is thereafter wound in a coil or on a spool, reel, or the like. The fasteners will be cut into individual components at the time of diaper fabrication.

Figure 8:
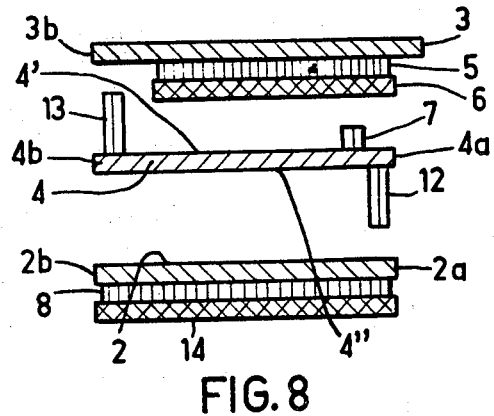

FIG. 8 elucidates the fabrication of a fastener such as shown in FIG. 5. A row of glue 12 is deposited on side 4" of a strip 4 near the lengthwise edge 4a, then two rows of glue 7 and 13 are deposited on side 4' near the lengthwise edges 4a and 4b. Thereupon the prepasted strip is combined with two paper tapes 3 and 2 each coated with pressure-sensitive adhesives 5 and 8, respectively, and protected by silicone-treated papers 6 and 14; and the laminated structure so obtained is wound in a coil, or on a spool, reel, or the like. The fasteners are cut into individual components when fabricating the diapers and are fixed thereto by applying adhesive zone 8 (after removing the protection 14) on the front part of the diaper. Alternatively, since the laminated structures are wound in coils, on spools, on mandrils, or the like, and then cut into individual fasteners for application to a diaper, the protection paper 14 may be eliminated. It is sufficient that the upper side of zone 3 be treated with a silicone compound. When winding the material, the adhesive layer 8 comes into contact with the silicone-treated side of zone 3. Furthermore, the loss of the first revolution of the material can be avoided by using a silicone-treated mandril.

Many variations may be made in the proposed fastener without departing from the inventive concept and the scope of the invention. In particular zone 2 of the fastener can comprise a thermosetting material and may be hot-fixed to the support sheet of the diaper. The aforesaid and other modifications, being within the skill of the art, are to be included in the present invention, which is limited solely by the appended claims.

It is claimed:

1. A fastener in the shape of an "S" to be affixed to a disposable diaper during the manufacturing process of the diaper comprising a first end zone, a central elastic zone, and a second end zone; the side of said second zone facing the central zone being coated with a pressure-sensitive adhesive which in turn is covered with a protective element and connected to said central zone by a continuous or discontinuous row of glue parallel to the folds of said fastener.

2. The fastener according to claim 1 wherein the side of the protective element in contact with the pressure-sensitive adhesive is treated with a silicone compound.

3. The fastener according to claim 1 wherein the attachment between the protective element and the central zone is stronger than the attachment between the protective element and the second zone.

4. The fastener according to claim 1 wherein the side of the first zone opposite the side facing the central zone is coated with a pressure-sensitive adhesive.

5. The fastener according to claim 1 wherein said central zone is connected to said first zone by dots and/or rows of glue so arranged in order that said zones are kept parallel.

6. The fastener according to claim 5 wherein the bonding between the distinct elements of the fastener is stronger than the bonding of the rows of glue maintaining the first and central zones parallel.

7. The fastener according to claim 1 wherein only the median part of the side of the second zone facing the central zone is coated with a pressure-sensitive adhesive.

8. The fastener according to claim 1 wherein the length of the second zone exceeds the length of the first zone.

9. The fastener according to claim 1 wherein the various zones consist of an elastic strip.

10. The fastener according to claim 1 characterized in that the first and second zones are made of paper and the central zone is an elastic band.

11. The fastener according to claim 1 wherein the first zone, the central zone, and the second zone, respectively, are distinct elements connected to each other by rows of glue.

12. The fastener according to claim 11 wherein the rows of glue are arranged on the sides opposite to the central zone near its lateral edges.

13. The fastener according to claim 11 wherein the rows of glue are arranged on the same side of the central zone near its lateral edges.

14. The fastener according to claim 13 wherein one lateral edge of the central zone is glued to a bend-back end of the first zone.

15. The fastener according to claim 13 wherein the side of the first zone facing the central zone is treated with a silicone-containing compound.

16. Process for the manufacture of a fastener comprising the sequential steps of
(a) applying a single row of glue to one side of an elastic strip near one lateral edge;
(b) applying a row of glue to the opposite side of the strip treated in (a) adjacent each lengthwise edge;
(c) combining the strip treated in (b) with first and second paper tapes coated with a pressure-sensitive adhesive, said adhesive being covered with a protective element; the side of said strip provided with a single row of glue coming into contact with the side of the first paper tape without adhesive, and the side of said strip with two rows of glue coming into contact with the protective element covering the coated side of the second paper tape;
(d) winding said layered material of (c); and
(e) cutting the layered material of (d) into a series of fasteners when manufacturing diapers and applying said fasteners to diapers.

17. Process for the manufacture of a fastener comprising the steps of
(a) applying three rows of glue to one side of an elastic strip whereby
a first row is adjacent a lengthwise edge,
a second row is adjacent the first row, and
a third row is adjacent the other lengthwise edge;
(b) applying a row of glue to the other side of the strip treated in (a) adjacent to the lengthwise edge, on that side where said strip is provided only with one row of glue;
(c) combining the strip treated in (b) with first and second paper tapes of which one side is coated with a pressure-sensitive adhesive, said adhesive being covered with a protective element so that each lengthwise edge of the strip is respectively fixed to the edge of one paper tape on the side coated with a pressure-sensitive adhesive;
(d) folding the structure obtained in (c) into an "S"; and
(e) cutting the layered structure obtained in (d) into a series of fasteners at the time of diaper manufacture and applying said fasteners to diapers.

18. In combination a disposable diaper comprising an absorbing material including a padding of cellulosic fibers placed between an impermeable support sheet and a permeable non-woven material; and an S-shaped adhesive fastener comprising a first end zone, a central elastic zone, and a second end zone; the side of said second zone facing the central zone being coated with a pressure-sensitive adhesive which in turn is covered with a protective element and connected to said central zone by a continuous or discontinuous row of glue parallel to the folds of said fastener, said first end being firmly fixed to the support sheet at its upper end.

* * * * *